(12) United States Patent
Tsuji et al.

(10) Patent No.: US 7,056,499 B2
(45) Date of Patent: Jun. 6, 2006

(54) TREATING METHOD FOR SUPPRESSING HAIR GROWTH

(75) Inventors: Naoko Tsuji, Haga-gun (JP); Shigeru Moriwaki, Haga-gun (JP); Atsushi Ohuchi, Haga-gun (JP); Yasuto Suzuki, Haga-gun (JP)

(73) Assignee: Kao Corporation, Tokyo (JP)

(*) Notice: Subject to any disclaimer, the term of this patent is extended or adjusted under 35 U.S.C. 154(b) by 485 days.

(21) Appl. No.: 10/067,941

(22) Filed: Feb. 8, 2002

(65) Prior Publication Data

US 2002/0146404 A1 Oct. 10, 2002

Related U.S. Application Data

(63) Continuation of application No. 09/614,166, filed on Jul. 11, 2000, now Pat. No. 6,375,948.

(30) Foreign Application Priority Data

Jul. 12, 1999 (JP) .............................. 11-197811
Feb. 17, 2000 (JP) .......................... 2000-39673

(51) Int. Cl.
*A61K 7/06* (2006.01)
*A61K 38/54* (2006.01)
*A61K 38/48* (2006.01)
*A61K 38/46* (2006.01)
*A01N 57/00* (2006.01)

(52) U.S. Cl. .................. 424/70.1; 424/94.2; 424/94.21; 424/94.64; 424/94.65; 424/94.66; 514/100

(58) Field of Classification Search ............... 424/70.1, 424/74, 94.2, 94.21, 94.64, 94.65, 94.66, 424/750; 514/100

See application file for complete search history.

(56) References Cited

U.S. PATENT DOCUMENTS

| | | |
|---|---|---|
| 3,623,950 A | 11/1971 | Monsheimer et al. |
| 3,694,547 A | 9/1972 | Forsthoff |
| 3,840,433 A | 10/1974 | Aunstrup et al. |
| 4,431,582 A | 2/1984 | Stenn |
| 4,636,222 A | 1/1987 | Pfleiderer et al. |
| 4,933,177 A | 6/1990 | Grollier et al. |
| 5,057,502 A | 10/1991 | Walsh |
| 5,196,534 A | 3/1993 | Whitehead et al. |
| 5,217,994 A | 6/1993 | Egbertson et al. |
| 5,294,616 A | 3/1994 | Duggan et al. |
| 5,338,747 A | 8/1994 | Robert et al. |
| 5,376,637 A | 12/1994 | Sawai et al. |
| 5,391,466 A | 2/1995 | Ueda et al. |
| 5,750,702 A | 5/1998 | Albaugh et al. |
| 5,766,633 A | 6/1998 | Milstein et al. |
| 6,075,052 A | 6/2000 | Suzuki et al. |
| 6,113,926 A | 9/2000 | Soler et al. |
| 6,114,336 A | 9/2000 | Blanc-Ferras et al. |
| 6,171,595 B1 | 1/2001 | Suzuki et al. |
| 6,203,791 B1 * | 3/2001 | Protopapa et al. |
| 6,407,056 B1 * | 6/2002 | Seiberg et al. |

FOREIGN PATENT DOCUMENTS

| | | | |
|---|---|---|---|
| CS | 182382 | * | 3/1980 |
| DE | 19649098 | * | 5/1998 |
| EP | 532219 | | 3/1993 |
| EP | 0622069 A1 | | 11/1994 |
| FR | 2709952 A1 | | 3/1995 |
| JP | 402004707 A | | 1/1990 |
| JP | HEI 10-17460 | | 1/1998 |
| JP | 10324612S A2 | * | 12/1998 |
| WO | WO 95/07924 | | 3/1995 |
| WO | WO 97/05887 | | 2/1997 |
| WO | WO 98/02134 | * | 1/1998 |
| WO | WO 98/25580 | * | 6/1998 |

OTHER PUBLICATIONS

Chemical Abstracts, AN 125: XP–002133265.
Journal of Medicinal Chemistry, vol. 33, No. 1, pp. 263–273, Phosphoramidate Peptide Inhibitors of Human Skin Fibroblast Collagenase, Zbigniew P. Kortylewicz and Richard E. Galardy.

* cited by examiner

*Primary Examiner*—Christopher R. Tate
*Assistant Examiner*—Michele C. Flood
(74) *Attorney, Agent, or Firm*—Oblon, Spivak, McClelland, Maier & Neustadt, P.C.

(57) ABSTRACT

The present invention relates to a treating method for hair growth inhibition, which comprises administering (A) the extract of a plant of the family Juniperus or a malt. In addition, the present invention relates to a dermatologic composition for external use, which comprises (B) an elastase inhibitor or neutral endopeptidase inhibitor, and the above-described component (A) and/or (C) at least one proteolytic enzyme selected from the group consisting of papain, trypsin, chymotrypsin, pepsin, bromelain, ficin and pancreatin.

8 Claims, No Drawings

TREATING METHOD FOR SUPPRESSING HAIR GROWTH

TECHNICAL FIELD

The present invention relates to a treating method and a dermatologic composition for external use, each for suppressing hair growth.

BACKGROUND ART

Although the body hair serves to biologically protect important organs such as head, chest, hands and feet, the organ-protecting function of the hair is losing its importance with the appearance and development of protecting means such as clothes and protectors.

The hair was so far desired to be abundant. in recent years, however, the hair, particularly, that of hands and feet tends to be undesired from the aesthetic viewpoint. To meet such a tendency, various body hair removing methods have been developed and utilized. Specific examples include a mechanical removing method using a shaver, hair-tweezers or the like and, a method of rooting up the hair by using a depilatory and a method making use of the chemical action of a hair removing agent (EP-622069A1, WO97/44005).

These hair removing methods however give a physical or chemical stimulus to the skin. In addition, their effects do not last permanently, though there is a little difference in durability among the methods, which needs the hair removing treatment again after the passage of a predetermined time. There is accordingly a demand or reducing the frequency of the hair removing treatment.

An object of the present invention is therefore to provide a treating method for hair growth inhibition which method is capable of effectively suppressing the growth of the body hair, thereby decreasing the removing frequency of the body hair.

DISCLOSURE OF THE INVENTION

The present inventors have carried out an extensive investigation. As a result, it has been found that a specific plant extract has excellent hair growth inhibitory effects and a dermatologic composition for external use which comprises it is useful as a hair growth inhibitor.

In one aspect of the present invention, there is thus provided a treating method for hair growth inhibition, which comprises administering an extract of the plant belonging to the family of Juniperus or a malt extract.

In another aspect of the present invention, there is also provided a dermatologic composition for external use, which comprises (A) an extract of the plant belonging to the family of Juniperus or a malt extract, (B) an elastase inhibitor or neutral endopeptidase inhibitor.

In a further aspect of the present invention, there is also provided a dermatologic composition for external use, which comprises (A) an extract of the plant belonging to the family of Juniperus or a malt extract, (B) an elastase inhibitor or neutral endopeptidase inhibitor, and (C) at least one proteolytic enzyme selected from the group consisting of papain, trypsin, chymotrypsin, pepsin, bromelain, ficin and pancreatin.

In a still further aspect of the present invention, there is also provided a dermatologic composition for external use, which comprises (B) an elastase inhibitor or neutral endopeptidase inhibitor, and (C) at least one proteolytic enzyme selected from the group consisting of papain, trypsin, chymotrypsin, pepsin, bromelain, ficin and pancreatin.

In a still further aspect of the present invention, there is also provided a treating method for hair growth inhibition, which comprises administering a composition containing the above-described components (A) and (B), a composition containing the above-descried components (A), (B) and (C), or a composition containing the above-described components (B) and (C).

BEST MODES FOR CARRYING OUT THE INVENTION

Examples of the plant belonging to the family of Juniperus and usable in the present invention include *Juniperus communis, Juniperus virginiana* L., *Juniperus morrisonicola* Hayata and *Juniperus formosana* Hayata. Of these, *Juniperus communis* and *Juniperus virginiana* L. are particularly preferred. These plants of the family of Juniperus are preferably extracted at the leave or fruit portion thereof.

As a malt, that of wheat, barley, rye or oats is used.

The term "extract of a plant" as used herein means a solvent extract available by extracting the above-described portion of the plant in a solvent or through an extracting device such as Soxhlet extractor, or its dilute solution, concentrate or dry powder.

Examples of the solvent used for extraction include water, alcohols such as methanol, ethanol, propanol and butanol, polyhydric alcohols such as polypropylene glycol and butylene glycol, ketones such as acetone and methyl ethyl ketone, esters such as methyl acetate and ethyl acetate, linear or cyclic ethers such as tetrahydrofuran and diethyl ether, halogenated hydrocarbons such as dichloromethane, chloroform and carbon tetrachloride, hydrocarbons such as hexane, cyclohexane and petroleum ether, aromatic hydrocarbons such as benzene and toluene, polyethers such as polyethylene glycol, and pyridines. They may be used either singly or in combination.

From the above-described extract, inactive impurities can be removed by a technique such as liquid-liquid partition or solvent-adding precipitation. In the present invention, it is preferred to use such a purified extract. If necessary, the extract may be used after deodorization or decoloring in a known manner.

Although there is no particular limitation imposed on the form of the hair growth suppressing composition of the present invention, it is preferred to formulate it as a hair-removing, depilatory or shaving cosmetic composition. Specific examples of such a cosmetic composition include hair removers in the form of a paste, cream or aerosol, depilatories in the form of a wax, jelly or sheet, agents in the form of a lotion or cream used for treatment after hair removal or depilation, pre-shaving agents such as pre-shaving lotion, shaving agents such as shaving cream, and after-shaving agents such as after-shaving lotion.

The above-described effective component is preferably contained in the hair growth inhibiting composition of the present invention in an amount of 0.00001 to 50 wt. %, particularly 0.0001 to 10 wt. %, as a dry solids content, from the viewpoints of the hair growth inhibitory effects and economy.

In the present invention, it is possible to use, together with the component (A), an elastase inhibitor and/or neutral endopeptidase inhibitor (B) and by using them in combination, the resulting dermatologic composition for external use has more improved hair growth inhibitory effects.

The "elastase" as used herein means one of proteolytic enzymes which are presumed to play an important role for metabolism in the tissues of the living body. It is known that the neutrophilic elastase closely relates to the protection from infection or decomposition and regeneration of the damaged tissue, while the dermal-fibroblast-derived elastase takes part in the aging of the skin. The term "elastase inhibitor" as used herein embraces respective substances having inhibitory activity against these elastases. Particularly preferred are substances inhibiting dermal-fibroblast-derived elastase, for example, those exhibiting inhibitory activity of at least 50% in the concentration of 1 mM in an enzyme activity measuring system which contains an enzyme solution extracted from cultured human fibroblast with 0.1% Triton X-100/0.2M tris-HCl buffer (pH 8.0) and, as a substrate, N-succinyl-Ala-Ala-Ala-p-nitroanilide.

Examples of such an elastase inhibitor include (1) phosphonic acid derivatives as described in Japanese Patent Application Laid-Open No. HEI 10-324611, (2) mercaptopropionic amide derivatives as described in Japanese Patent Application Laid-Open No. HEI 10-265360, and (3) plants selected from ginger rhizome, hydrolyzed almond, birch, clove, rose hip, hawthorn, white birch and gambir or extracts, steam distillates or pressed products thereof.

The above-described phosphonic acid derivatives mean the phosphonic acid derivatives represented by the following formula (1):

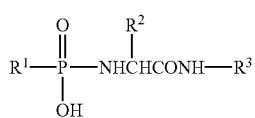

(1)

(wherein, $R^1$ represents a hydrogen atom, a hydroxyl group, a substituted or unsubstituted hydrocarbon group or a substituted or unsubstituted saccharide residue, $R^2$ represents a hydrogen atom, a substituted or unsubstituted hydrocarbon group or a substituted or unsubstituted saccharide residue, and $R^3$ represents a hydrogen atom or —CH($R^4$)COOH (in which, $R^4$ representing a hydrogen atom or a substituted or unsubstituted hydrocarbon group), or salts thereof.

As the substituted or unsubstituted hydrocarbon group represented by $R^1$, $R^2$ or $R^4$ in the above-described formula (1), either a saturated hydrocarbon group or an unsaturated hydrocarbon group can be used and examples include alkyl, alkenyl, alkynyl, cyclic alkyl, cyclic alkenyl, aromatic hydrocarbon and aralkyl groups. These hydrocarbon groups each preferably has 1 to 24 carbon atoms, particularly 1 to 18 carbon atoms.

Among the above-exemplified hydrocarbon groups, alkyl, cyclic alkyl, aromatic hydrocarbon and aralkyl groups are preferred. Preferred examples of the alkyl group include linear or branched $C_{1-12}$ alkyl groups, with n-propyl, isopropyl, n-butyl, isobutyl, tert-butyl and isoamyl groups being more preferred. Preferred examples of the cyclic alkyl group include 5- to 7-membered alicyclic alkyl groups, with cyclopentyl and cyclohexyl groups being more preferred. Preferred examples of the aromatic hydrocarbon group include $C_{6-14}$ aromatic hydrocarbon groups such as phenyl and naphthyl. Preferred examples of the aralkyl group include $C_{1-5}$ alkyl groups each substituted with a $C_{6-12}$ aromatic hydrocarbon group, such as 2-phenylethyl (=phenethyl), 2-(1-naphthyl)ethyl and 2-(2-naphthyl)ethyl groups.

Examples of the group substitutable for these hydrocarbon groups include halogen atoms, a hydroxy group, alkoxy groups, acyl groups, protected or unprotected amino groups and heterocyclic groups. Examples of the halogen atom include chlorine, bromine and iodine. As the alkoxy groups, $C_{1-12}$ alkoxy groups such as methoxy, ethoxy and isopropoxy are preferred. As the acyl groups, $C_{1-12}$ alkanoyl groups such as acetyl, propionyl and butyryl groups are preferred. Examples of the protected or unprotected amino groups include amino, acylamino, alkylamino and dialkylamino groups. As the heterocyclic group, preferred are 5- to 14-membered monocylic or fused cyclic groups having 1 to 3 hetero atoms such as nitrogen, oxygen and/or sulfur, for example, pyridyl, pyridazinyl, furyl, thienyl, indolyl, thiazolyl, imidazolyl, benzofuryl and benzothienyl groups.

Examples of the saccharide residue include monosaccharide residue and oligosaccharide residue. Examples of the group substitutable for these saccharide residues include alkyl, acyl and aralkyl groups. As the alkyl, acyl and aralkyl groups, those exemplified above can be mentioned.

These phosphonic acid derivatives can be prepared, for example, in accordance with the process as described in Japanese Patent Application Laid-Open No. HEI 5-105698.

The above-described mercaptopropionic amide derivatives mean mercaptopropionic amide derivative represented by the following formula (2):

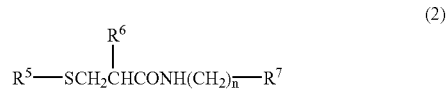

(2)

(wherein, $R^5$ represents a hydrogen atom or an acyl group, $R^6$ represents a hydrogen atom or a substituted or unsubstituted hydrocarbon group, $R^7$ represents a hydrogen atom, a carboxyl group, an alkoxycarbonyl group, a substituted or unsubstituted hydrocarbon group, a substituted or unsubstituted heterocyclic group or an acyl group and n stands for 1 to 20) or salts thereof.

As the acyl group represented by $R^5$ or $R^7$ in the above-described formula (2), alkanoyl groups and arylcarbonyl groups can be mentioned. As the alkanoyl groups, $C_{1-12}$ alkanoyl groups such as acetyl, propionyl and butyryl groups are preferred, while as the arylcarbonyl groups, $C_{7-15}$ arylcarbonyl groups such as benzoyl, substituted benzoyl, naphthylcarbonyl and substituted naphthylcarbonyl groups are preferred. Examples of the group substitutable for the benzoyl or naphthylcarbonyl group include alkyl, alkoxy, halogen, amino, hydroxy and alkanoyloxy groups.

As the substituted or unsubstituted hydrocarbon group represented by $R^6$ or $R^7$, those exemplified above as $R^1$, $R^2$ or $R^4$ can be mentioned.

As the heterocyclic group represented by $R^7$, 5- to 14-membered monocylic or fused ring groups each having 1 to 3 hetero atoms such as nitrogen, oxygen and/or sulfur are preferred. Specific examples include pyridyl, pyridazinyl, furyl, thienyl, indolyl, thiazolyl, imidazolyl, benzofuryl, benzothienyl, pyrrolidinyl, piperidinyl, morpholinyl and piperazinyl groups. Examples of the group substitutable for these heterocyclic groups include halogen atoms, hydroxyl group, alkoxyl groups, acyl groups and protected or unprotected amino groups. As the specific examples of these substituents, those exemplified above as the substituent for the hydrocarbon group of $R^1$, $R^2$ or $R^4$ can be mentioned.

Examples of the alkoxycarbonyl group represented by $R^7$ include $C_{1-12}$ alkoxycarbonyl groups, more specifically, methoxycarbonyl, ethoxycarbonyl, isopropoxycarbonyl and butoxycarbonyl groups.

These mercaptopropionic amide derivatives can be prepared, for example, in accordance with the process as described in Japanese Patent Application Laid-Open No. SHO 57-24354.

The following are the typical compounds of the above-described phosphonic acid derivatives and mercaptopropionic amide derivatives.

Compound 1
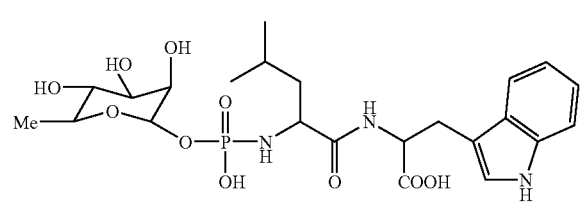

Compound 2
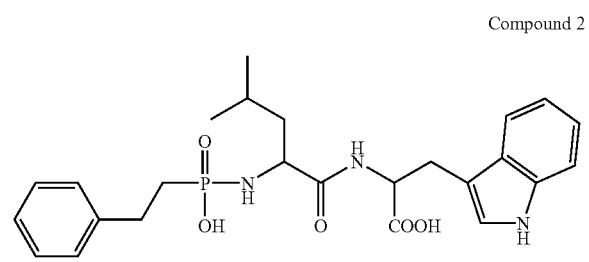

Compound 3
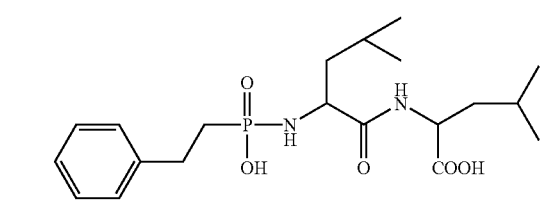

Compound 4
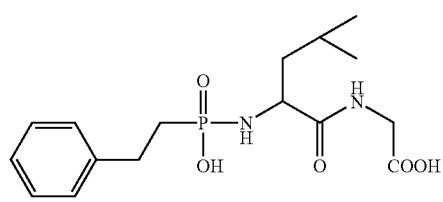

Compound 5
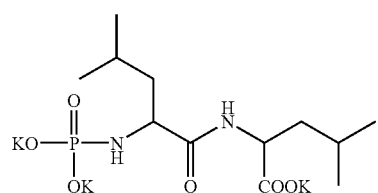

Compound 6
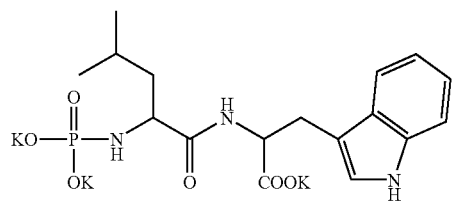

Compound 7
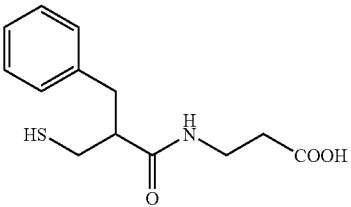

In the present invention, the ginger rhizome (Zingiberis Rhizoma) means an underground stem of ginger (*Zingiber officinale* Roscoe) of the family Zingiberaceae; the hydrolyzed almond means a mixture available by hydrolyzing, in the presence of an acid or alkali, the seed (sweet seed) of almond (*Prunus amygdalus* Batsch) of the family Rosaceae, the clove means a bud of a clove (*Syzygium aromaticum* Merrill et Perry (*Eugenia caryophyllata* Thunberg)), the rose hip means a fruit of a wild rose (*Rosa multiflora* Thunberg) of the family Rosaceae or plants analogous thereto, the hawthorn means a terrestrial part of a hawthorn (*Craegus oxyacantha* L.) of the family Rosaceae, the white birch means a leave, bark, or wood part of European birch (*Betula alba* L.) of the family Butulaceae, and the gambir means a dried and solidified aqueous extract prepared from the leaves or young twigs of *Uncaria gambir* Roxburgh of the family Rubiaceae. These plants have conventionally been used as a crude drug or food and are excellent in safety.

The term "plant extract" as used herein, except the hydrolyzed almond, means a solvent extract available by extracting the above-described plant in the pulverized form with a solvent at room temperature or under heating, or extracting by an extractor such as Soxhlet extractor; or a diluted solution, concentrate or dry powder thereof.

In the present invention, it is possible to use plants as are or after extraction, steam distillation or pressing. Examples of the solvent usable for extraction include water, alcohols such as methanol, ethanol, propanol and butanol, polyhydric alcohols such as propylene glycol and butylene glycol, ketones such as acetone and methyl ethyl ketone, esters such as methyl acetate and ethyl acetate, linear or cyclic ethers such as tetrahydrofuran and diethyl ether, halogenated hydrocarbons such as dichloromethane, hydrocarbons such as hexane, cyclohexane and petroleum ether, aromatic hydrocarbons such as toluene, polyethers such as polyethylene glycol and pyridines. They may be used either singly or in combination.

On the other hand, the hydrolyzed almond can be obtained, for example, by adding 0.1 to 20 vol. % of an acid such as sulfuric acid, hydrochloric acid, acetic acid or phosphoric acid or 0.01 to 10N alkali such as sodium hydroxide or potassium hydroxide to a solvent such as water, ethanol, propanol, butanol, propylene glycol or 1,3-butylene glycol, preferably water or ethanol, dipping an almond in the resulting mixture usually at 3 to 100° C. and then removing an insoluble matter. The insoluble matter is preferably removed after adjustment of the pH to about 7.0 with an alkali such as sodium hydroxide, potassium hydroxide, sodium carbonate or sodium bicarbonate, or an acid such as sulfuric acid, hydrochloric acid, acetic acid or phosphoric acid. As the solvent, a mixture of at least two solvents may be used.

The above-described extracts can be used after removing therefrom inactive impurities by a technique such as liquid-liquid partition or solvent-adding precipitation and if necessary, subjecting the residue to deodorization or decoloring in a known manner. Moreover, it is possible to use the extracts as a more active fraction obtained by fractionation through suitable separating means such as gel filtration, chromatography or precision distillation.

Neutral endopipetidase is an enzyme for decomposing opioid peptides such as enkephalins or neuropeptides such as substance P and bradykinin. Although the inhibitor against this enzyme is known to be useful as a substitute for a morphine type substance, that is, as an analgesic, there is no report suggesting the relation between the activity of this enzyme and growth of the body hair.

As the neutral endopeptidase inhibitor to be used in the present invention, a dermal-fibroblast-derived neutral endopeptidase inhibitor is preferred. Examples of such an inhibitor include substances each exhibiting at least 50 inhibitory activity in the concentration of 1 mM in an enzymatic activity measuring system obtained by adding, to an MES buffer (100 mM, pH 6.5) added with sodium chloride (300 mM), an enzyme solution extracted from the cultured human fibroblast with a 0.1 Triton X-100/0.2 M tris-HCl buffer (pH 8.0) and glutaryl-Ala-Ala-Phe-4-methoxy-2-naphthylamine as a substrate.

Examples of the neutral endopeptidase inhibitor include the compounds represented by the following formulas (a) to (g).

(a) Malonic amide derivatives represented by the formula (a) and salts thereof:

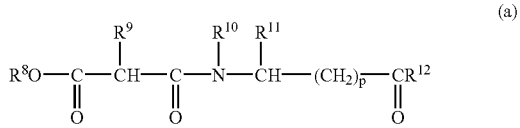

[wherein, $R^8$ represents a hydrogen atom, an alkyl group, an alkenyl group or an aralkyl group;

$R^9$ represents a hydrogen atom or a substituted or unsubstituted alkyl, alkenyl or aralkyl group, $R^{10}$ represents a hydrogen atom, an alkyl group or an alkenyl group, or may be coupled with $R^{11}$ to form a heterocycle with the adjacent nitrogen atom, $R^{11}$ represents a hydrogen atom, or a substituted or unsubstituted alkyl, alkenyl or aralkyl group, or may be coupled with $R^{10}$ to form the above-described heterocycle, $R^{12}$ represents a hydroxyl group, an alkoxy group, an alkenyloxy group or an amino acid residue, and p stands for an integer of 0 to 5].

(b) Hydroxamic acid derivatives represented by the formula (b) and salts thereof (Japanese Patent Application Laid-Open No. Sho 58-77852).

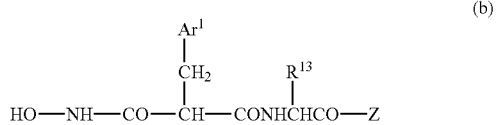

(wherein, $Ar^1$ represents a substituted or unsubstituted phenyl group, $R^{13}$ represents a hydrogen atom, an alkyl group or a methylthioalkyl group, and Z represents a hydroxy, alkoxy, aralkyloxy, phenoxy, amino, alkylamino or dialkylamino group).

(c) Mercaptopropionylamide derivatives represented by the formula (c) and salts thereof (Japanese Patent Application Laid-Open No. Sho 60-1366554).

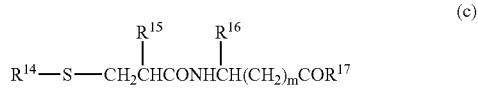

(wherein, $R^{14}$ represents a hydrogen atom or an acyl group, $R^{15}$ represents an aralkyl or heteroaralkyl group, $R^{16}$ represents a hydrogen atom or an alkyl, aralkyl or heteroaralkyl group, $R^{17}$ represents a hydroxy, alkoxy, aralkyloxy, heteroaralkyloxy, amino, alkylamino or dialkylamino group and m stands for 1 to 15).

(d) N-substituted butylamide derivatives represented by the formula (d) and salts thereof (Japanese Patent Application Laid-Open No. Sho 61-502468).

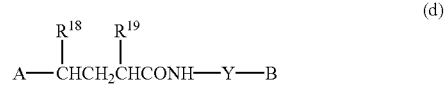

(wherein, A and B each independently represents a hydroxymethyl, carboxyl, esterified carboxyl, carbamoyl or N-substituted carbamoyl group, $R^{18}$ and $R^{19}$ each independently represents an alkyl, aryl, heteroaryl or aralkyl group and Y represents a substituted or unsubstituted alkylene group).

(e) Hydroxamic acid derivatives represented by the formula (e) and salts thereof (Japanese Patent Application Laid-Open No. Sho 63-101353).

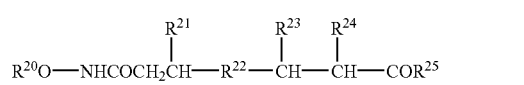

(wherein, $R^{20}$ represents a hydrogen atom or an acyl group, $R^{21}$ and $R^{23}$ each independently represents a hydrogen atom, an alkyl group or an aralkyl group, $R^{22}$ represents CONH or NHCO, $R^{24}$ represents a hydrogen atom or an amino group and $R^{25}$ represents a hydroxy, alkoxy, amino or N-substituted amino group).

(f) Dipeptides represented by the formula (f):

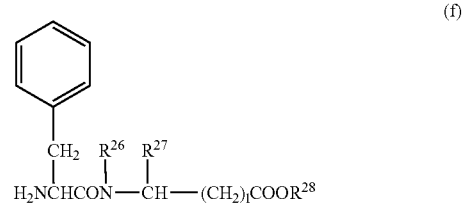

[wherein, $R^{26}$ represents a hydrogen atom or an alkyl group or may be coupled with $R^{27}$ to form a heterocycle together with the adjacent nitrogen atom, $R^{27}$ represents a hydrogen atom or a substituted or unsubstituted alkyl or aralkyl group, or may be coupled with $R^{26}$ to form the above-described heterocycle, $R^{28}$ represents a hydrogen atom or an alkyl, alkenyl or aralkyl group, and l stands for an integer of 0 to 4].

(g) Dipeptides represented by the formula (g):

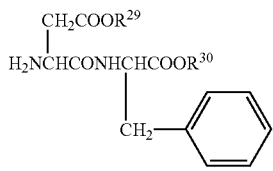

(wherein, $R^{29}$ and $R^{30}$ each independently represents a hydrogen atom or an alkyl or aralkyl group).

In the above-described formulas (a) to (g), the alkyl part of the alkyl, alkoxy, alkyloxy or methylthioalkyl group preferably has 1 to 6 carbon atoms. As the aralkyl group, phenyl ($C_{1-6}$ alkyl) groups are preferred. As the heteroaralkyl group, heteroaryl($C_{1-6}$ alkyl) groups are preferred, with pyridyl($C_{1-6}$ alkyl), pyrimidinyl($C_{1-6}$ alkyl) and purine($C_{1-6}$ alkyl) groups being particularly preferred. As the alkylene group, those having 1 to 8 carbon atoms are preferred.

As the aryl group, phenyl and naphthyl groups are preferred. As the aralkyloxy group, phenyl(($C_{1-6}$ alkyl) groups are preferred. As the heteroaralkyloxy group, heteroaryl ($C_{1-6}$ alkyl)oxy groups are preferred, with pyridyl($C_{1-6}$ alkyl)oxy, pyrimidinyl($C_{1-6}$ alkyl)oxy and purine($C_{1-6}$ alkyl) oxy groups being particularly preferred. As the alkenyl group, those having 2 to 6 carbon atoms are preferred. Examples of the substituent for the alkyl, aralkyl or phenyl group include carboxyl group, halogen atoms and alkoxy groups. Examples of the heterocycle formed by $R^{10}$ and $R^{11}$ or $R^{26}$ and $R^{27}$ include pyrrolidine and piperidine rings.

Among them, the malonic acid amide derivatives of the formula (a) and dipeptides of each of the formula (f) and (g) are particularly preferred.

As the alkyl or alkenyl group in $R^8$ or $R^{10}$ of the formula (a), those having 1 to 8 carbon atoms are preferred, of which those having 1 to 4 carbon atoms are particularly preferred and alkyl groups having 1 to 4 carbon atoms are more preferred. Among them, methyl, ethyl, n-propyl, isopropyl-, n-butyl, isobutyl and t-butyl groups are particularly preferred. Examples of the aralkyl group include phenylalkyl, biphenylalkyl and naphthylalkyl groups, of which the phenyl($C_{1-6}$ alkyl) groups, particularly benzyl group, are preferred.

As $R^8$, a hydrogen atom, $C_{1-8}$ alkyl groups and phenyl ($C_{1-6}$ alkyl) groups are particularly preferred.

As $R^{10}$, a hydrogen atom is most preferred.

As $R^9$ or $R^{11}$, a hydrogen atom, linear or branched $C_{1-12}$ alkyl or alkenyl groups and aralkyl groups are preferred, of which the hydrogen atom and linear or branched $C_{3-6}$ alkyl or alkenyl groups are more preferred, and the hydrogen atom, n-propyl group, isopropyl group, isobutyl group and tert-butyl group are particularly preferred. Examples of the aralkyl group include phenylalkyl and naphthylalkyl groups, of which the phenyl($C_{1-6}$ alkyl) groups are preferred, with the benzyl and phenetyl groups being more preferred.

Examples of the heterocycle formed by $R^{10}$ and $R^{11}$ include pyrrolidine and piperidine rings, of which the pyrrolidine ring is preferred.

As the alkoxy or alkenyloxy group in $R^{12}$, alkoxy or alkenyloxy groups having 1 to 8, particularly 1 to 4 carbon atoms are preferred, with the $C_{1-4}$ alkoxy groups being more preferred. Examples of the amino acid residue include essential amino acid residues. The amino group of this amino acid forms an amide bond with the carbonyl group in the formula (1). As $R^{12}$, a hydroxyl group and $C_{1-4}$ alkoxy groups are preferred, with hydroxyl, methoxy, ethoxy, n-propyloxy, isopropyloxy, n-butyloxy, isobutyloxy and t-butyloxy groups being particularly preferred.

As p, 0 or 1 is most preferred.

In the formula (f), a hydrogen atom is preferred as $R^{26}$. As $R^{27}$, a hydrogen atom and methyl, isopropyl, isobutyl, t-butyl, benzyl, phenethyl, carboxymethyl and carboxyethyl groups are preferred. As $R^{28}$, a hydrogen atom and methyl, ethyl, n-propyl, isopropyl, n-butyl, isobutyl, t-butyl and benzyl groups are preferred. As l, 0, 1 or 2 is preferred.

In the formula (g), $R^{29}$ preferably represents a hydrogen atom, while $R^{30}$ preferably represents a hydrogen atom or a methyl group.

Examples of the salts of the compounds of the formulas (a) to (g) include alkali metal salts, alkaline earth metal salts, amine salts, amino acid salts and acid addition salts. Preferred are alkali metal salts and amino acid salts. The compounds of the formulas (a) to (g) may have optical activity. Their steric configuration may be any one of R, S or racemic form, or they may be in a hydrated form.

Among the compounds represented by the formula (a), particularly preferred are as follows:

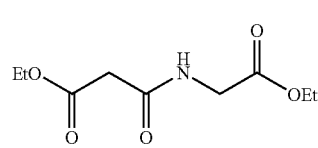

Compound 8

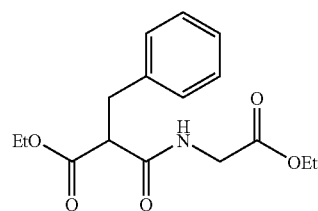

Compound 9

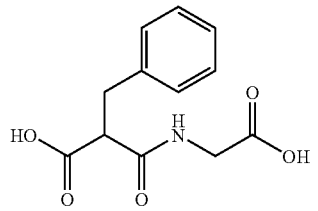

Compound 10

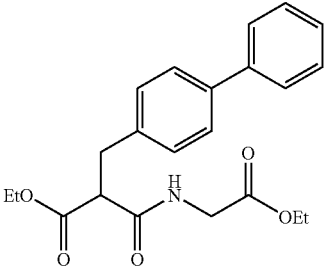

Compound 11

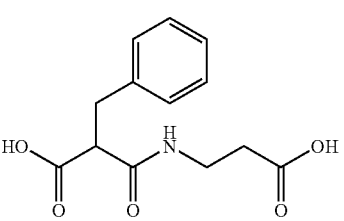

Compound 12

Compound 13

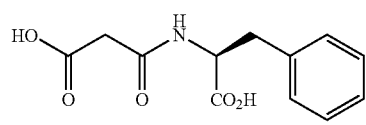

The compound represented by the formula (a) can be synthesized, for example, in accordance with the process of Nakano, et al. (Chem. Lett., 505–8(1990)) represented by the following reaction scheme:

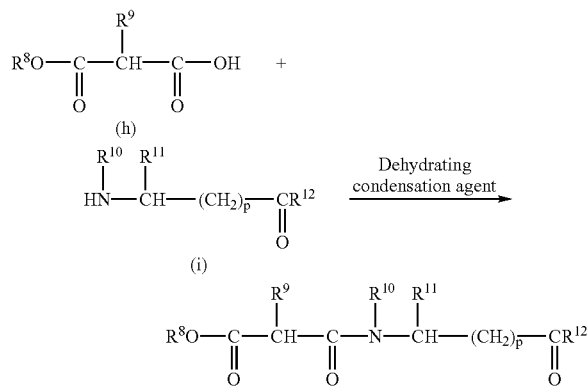

($R^8$ to $R^{12}$ and p have the same meanings as described above).

The target compound is obtained by reacting the malonic acid half ester (h) with the amino acid ester (i) in the presence of a dehydrating condensation agent and optionally reacting the resulting mixture with a base such as sodium hydroxide.

The compound represented by the formula (a) can also be synthesized in accordance with the below-described process of Katsuki, et al. (Bull. Chem. Soc. Jpn., 49, 3207–3290 (1976)).

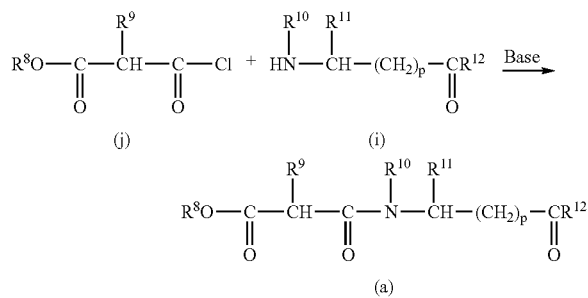

(wherein $R^8$ to $R^{12}$ and p have the same meanings as described above).

Described specifically, the target compound is obtained by reacting the malonic acid half ester acid chloride (j) with the amino acid ester (i) in the presence of a base and optionally alkylating the resulting mixture with an alkyl halide or hydrolyzing it with a base such as sodium hydroxide.

Examples of the dipeptide represented by the formula (f) include Phe-Gly, Phe-β-Ala, Phe-Phe, Phe-Leu, Phe-Ala and Phe-Asp. They can be synthesized, for example, by the process as described in K. Ienaga, K. Higashihara and H. Kimura, Chem. Pharma. Bull., 35, 1249–1254(1987). Examples of the dipeptide represented by the formula (7) include Asp-Phe-OMe (aspartame) and Asp-Phe. As the compound of the formula (f) or (g), commercially available one can also be used.

From the viewpoints of hair growth inhibitory effects and economy, the dermatologic external composition of the present invention usually contains the elastase inhibitor and/or neutral endopeptidase inhibitor in an amount of 0.00001 to 40 wt. %, particularly 0.0001 to 10 wt. %. If this component is an extract or the like, the above-described amount is in terms of dry solid powder.

The dermatologic composition for external use according to the present invention, which contains the components (A) and (B), further contains (C) at least one proteolytic enzyme selected from papain, trypsin, chymotrypsin, pepsin, bromelain, ficin and pancreatin.

The dermatologic composition for external use, which contains the component (B) and the above-described component (C), also has excellent hair growth inhibitory effects.

It is usually preferred to adjust the content of the proteolytic enzyme (component (C)) in the dermatologic external composition of the present invention to 0.00001 to 10 wt. %, particularly 0.0001 to 3 wt. % from the viewpoints of the hair growth inhibitory effects and economy.

The weight ratio of the component (B) to the component (C) in the composition of the present invention depends on the nature of them, but the (B):(C) weight ratio preferably falls within a range of from 10:1 to 1:20, particularly 1:1 to 1:2, from the viewpoint of the hair growth inhibitory effects.

The composition of the present invention can be prepared by mixing the components (B) and (C) in a conventional manner but it is possible to mix them after enclose them in a liposome to heighten the percutaneous absorption. Liposome can be prepared, for example, by a known manner with a phospholipid such as lecithin as a material ("Biomembrane", written by Robert B Gennis, pp.74–77, Springer Verlag Tokyo Co., Ltd. (1990)).

To the composition for inhibiting hair growth or dermatologic external composition according to the present invention, a keratolytic or a component having hair-growth controlling or depilatory action such as thioglycolic acid or a salt thereof can be added as needed, in addition to the above-described component. Examples of the keratolytic include lactic acid, bioprase, salicylic acid, glycolic acid, citric acid, malic acid, sulfur, resorcin, thioxolone, selenium disulfide and urea. Examples of the salt of thioglycolic acid include not only sodium salt, potassium salt, calcium salt and ammonium salt but also alkanolamine salts such as monoethanolamine, diethanolamine and triethanolamine. Calcium thioglycolate is particularly preferred. Each of these keratolytics, or thioglycolic acid or salts thereof is preferably added in an amount of 0.01 to 10 wt. %, particularly 0.05 to 5%.

In the composition of the present invention, various desired components usually employed for cosmetics, quasi-drugs or drugs are incorporated within a range not impairing the effects of the present invention. Examples of such desired components include purified water, ethanol, oil components, humectants, thickeners, antiseptics, emulsifiers, drug efficacy ingredients, powders, ultraviolet absorbers, colorants, perfumes and emulsion stabilizers. Use of the dermatologic external composition according to the present invention as a cosmetic composition, particularly, hair-growth-inhibitory cosmetic composition is preferred.

Examples of the oil component include liquid paraffin, vaseline, paraffin wax, squalane, bees wax, carnauba wax, olive oil, lanolin, higher alcohols, fatty acids, synthetic ester oils between a higher alcohol and fatty acid and silicone oil. Examples of the humectant include sorbitol, xylitol, glycerin, maltitol, propylene glycol, 1,3-butylene glycol, 1,4-butylene glycol, sodium pyrrolidonecarboxylate, lactic acid, sodium lactate, polyoxypropylene fatty acid ester and polyethylene glycol. Examples of the thickener include water-soluble polymers such as carboxyvinyl polymer, carboxymethyl cellulose, polyvinyl alcohol, carrageenan and gelatin, and electrolytes such as sodium chloride and potassium chloride. Examples of the antiseptic include urea, methyl paraben, ethyl paraben, propyl paraben, butyl paraben and sodium benzoate. Those of the emulsifier include nonionic surfactants such as polyoxyethylene alkyl ether, polyoxyethylene fatty acid ester, polyoxyethylene sorbitan fatty acid ester, glycerin fatty acid ester, polyglycerin fatty acid ester, polyoxyethylene glycerin fatty acid ester, polyoxyethylene hydrogenated castor oil and polyoxyethylene sorbitol fatty acid ester. Illustrative of the powder include talc, sericite, mica, kaolin, silica, bentonite, vermiculite, zinc powder, mica, mica titanium, titanium oxide, magnesium oxide, zirconium oxide, barium sulfate, red oxide, iron oxide and ultramarine.

The compositions of the present invention have excellent hair growth inhibitory effects and have a high degree of safety for human body.

EXAMPLES

The present invention will hereinafter be described more specifically by Examples. It should however be borne in mind that the present invention is not limited to or by these examples. The amount of a plant extract is indicated as a dry solids content.

Preparation Example 1
Preparation of a Juniperus Extract

The raw leaves of *Juniperus virginiana* L. (the Family Juniperus of Cupressaceae) of American growth were dipped in 45% ethanol for 3 to 5 days for extraction. The supernatant was filtered to obtain the extract of *Juniperus virginiana* L. The resulting extract was found to have a specific gravity as measured at 25° C. of 0.93±5% and a solid concentration of 1.24%.

Preparation Example 2
Preparation of a *Juniperus communis* Extract

A raw fruit of *Juniperus communis* (the Family Juniperus of Cupressaceae) was dipped in 50% ethanol for 3 to 5 days for extraction. The supernatant was filtered to obtain the extract of *Juniperus communis*. The resulting extract was found to have a solid concentration of 1.5%.

Preparation Example 3
Preparation of a Malt Extract

The raw malt of Gramineae wheat (*Triticum aestivum* L.) of American growth was dipped in 42% ethanol for 3 to 5 days. The supernatant was filtered to obtain the malt extract. The resulting extract was found to have a specific gravity as measured at 25° C. of 0.94±5% and a solid concentration of 2.71%.

Preparation Example 4
Preparation of a Ginger Rhizome Extract

A ginger rhizome was sliced. To 50 g of the sliced ginger rhizome, 500 mL of 50% ethanol was added to dip the former in the latter, followed by filtration, whereby the ginger rhizome extract solution was obtained. The resulting extract solution was concentrated. As a result, the solid content was found to be 2.59 g, meaning that the extract solution had the solid concentration of 0.52%.

Preparation Example 5
Preparation of a Hydrolyzed Almond Extract

The pulverized almond (50 g) was extracted under heating (60° C. for 2 hours) with 200 mL of 0.1 mol/L sulfuric acid. The mixture was then allowed to cool down and filtered, whereby the extract solution was obtained. After neutralization of the resulting extract solution with 0.2 mol/L sodium hydroxide, it was diluted with distilled water, whereby 500 g of the hydrolyzed almond extract solution was obtained. The evaporation residue was found to be 5.2 g.

Preparation Example 6
Preparation of a Burnet Extract

The burnet was sliced. To 50 g of the sliced burnet, 500 mL of water was added to dip the former in the latter, followed by filtration, whereby the burner extract solution was obtained. As a result of concentration, the solid content was found to be 2.68 g, meaning that the extract solution had a solid concentration of 0.54%.

Preparation Example 7
Preparation of a Clove Extract

The clove was sliced. To 50 g of the sliced clove, 500 mL of 95% ethanol was added to dip the former in the latter, followed by filtration, whereby a clove extract solution was obtained. As a result of concentration, the solid content was found to be 1.46 g, meaning that the extract solution had a solid concentration of 0.29%.

Preparation Example 8
Preparation of a Rose Hip Extract

The rose hip was sliced. To 50 g of the sliced rose hip, 500 mL of water was added to dip the former in the latter, followed by filtration, whereby a rose hip extract solution was obtained. As a result of concentration, the solid content was found to be 2.28 g, meaning that the extract solution had a solid concentration of 0.46%.

Preparation Example 9
Preparation of a Hawthorn Extract

The hawthorn was sliced. To 50 g of the sliced hawthorn was added 500 mL of 50% ethanol to dip the former in the latter, followed by filtration, whereby a hawthorn extract solution was obtained. As a result of concentration, the solid content was found to be 3.09 g, meaning that the extract solution had a solid concentration of 0.62%.

Preparation Example 10
Preparation of a White Birch Extract

The white birch was sliced. To 50 g of the sliced birch was added 500 mL of 50 ethanol to dip the former in the latter, followed by filtration, whereby a white birch extract solution was obtained. As a result of concentration, the solid content was found to be 3.13 g, meaning that the extract solution had a solid concentration of 0.63%.

Preparation Example 11
Preparation of a Gambir Extract

The gambir was sliced. To 5 g of the sliced gambir was added 100 mL of ethanol to dip the former in the latter, followed by filtration, whereby a gambir extract solution was obtained. As a result of concentration, the solid content was found to be 2.51 g, meaning that the extract solution had a solid concentration of 2.51%.

Synthesis Example 1
Synthesis of Compound 8

In 50 mL of chloroform were dissolved 16.05 g (114 mmol) of glycine ethyl ester hydrochloride and 23.27 g (228 mmol) of triethylamine, followed by ice cooling to 5° C. Without changing the temperature, 10.00 g (57 mmol) of ethylmalonic chloride was added dropwise to the resulting solution. After completion of the dropwise addition, the disappearance of the raw material was confirmed by thin layer chromatography and a 5% aqueous phosphoric acid solution was added to terminate the reaction. The organic layer was washed with distilled water and saturated saline, dried over anhydrous sodium sulfate and then distilled to remove the solvent. The residue was subjected to column chromatography and eluted with a mixed solvent of ethyl acetate and n-hexane. The solvent was then distilled off, whereby 9.40 g (yield: 76%) of Compound 1 was obtained.

NMR (DMSO-$d_6$) δ: 2.48–2.51 (m, 6H), 3.30 (d, 2H, J=9 Hz), 3.85 (d, 2H, J=6 Hz), 4.02–4.20 (m, 4H), 8.49 (t, 1H, J=5 Hz).

Synthesis Example 2

Synthesis of Compound 9

In 50 mL of dehydrated tetrahydrofuran was dissolved 5.00 g (23.0 mmol) of Compound 1. The resulting solution was added to a suspension of 1.10 g (27.6 mmol) of sodium hydride in 30 mL of tetrahydrofuran, followed by heating to 50° C. Benzyl bromide (3.74 g, 21.9 mmol) was slowly added dropwise and at the same temperature, stirring was conducted for 3 hours. Then, the reaction was terminated.

NMR (DMSO-$d_6$) δ: 1.16(t, 1H, J=7 Hz), 2.93–3.19(m, 2H), 3.71(t, 1H, J=7 Hz), 3.80(d, 2H, j=6 Hz), 4.06(q, 4H, j=7 Hz), 7.13–7.29(m, 5H), 8.61(t, 1H, J=6H).

Synthesis Example 3

Synthesis of Compound 10

In 30 mL of methanol was dissolved 3.00 g (9.8 mmol) of Compound 2, followed by the addition of a solution or 1.20 g (21.5 mmol) of potassium hydroxide (KOH) in 10 mL of water. The resulting mixture was stirred at room temperature for 2 hours and then, the reaction was terminated. After removal of methanol by distillation under reduced pressure, a 5% aqueous phosphoric acid solution was added to the residue and the crystals thus precipitated were collected by filtration. The resulting crystals were washed with water and then dried under reduced pressure, whereby 2.17 g (yield: 88%) of Compound 2 was obtained.

NMR (DMSO-$d_6$) δ: 2.90(m, 2H), 3.59(t, 1H, J=7 Hz), 3.74(d, 2H, J=6 Hz), 7.12–7.32(m, 5H), 8.37(t, 1H, J=6 Hz), 12.49(br.s, 2H).

Synthesis Examples 4 to 6

Compounds 11 to 13 were synthesized in a similar manner to Synthesis Examples 1 to 3 by using the amino acid ester and alkyl halide as shown in Table 1.

TABLE 1

| Synthesis Example | Synthesis process | Amino acid ester | Alkyl halide | Yield | NMR | |
|---|---|---|---|---|---|---|
| 4 | 2 | — | Bromo-biphenyl-methane | 61% | DMSO-$d_6$ | 1.14–1.25(m, 6H), 2.99–3.20(m, 2H), 3.77(t, 1H, J=8Hz), 3.87(d, 2H, J=8Hz), 3.98–4.19(m, 4H), 7.24–7.65(m, 9H), 8.63(t, 1H, J=5Hz) |
| 5 | 1,2,3 | β-alanine methyl ester hydrochloride | Benzyl bromide | 55% | DMSO-$d_6$ | 2.15–2.39(m, 2H), 2.90–3.09(m, 2H), 3.10–3.34(m, 2H), 3.54(t, 1H, J=8Hz), 7.00–7.35(m, 5H), 8.11(t, 1H, J=5Hz), 12.38(br.s, 2H) |
| 6 | 1,3 | L-phenylalanine methyl ester hydrochloride | — | 68% | DMSO-$d_6$ | 2.84–3.10(m, 2H), 3.17(s, 2H), 4.42–4.53(m, 1H), 7.09–7.35(m, 5H), 8.35(d, 1H, J=8Hz), 12.24(br.s, 2H) |

After cooling, a 5% aqueous phosphoric acid solution was added and the resulting mixture was extracted with 300 mL of ethyl acetate. The organic layer was washed with a saturated aqueous solution of sodium bicarbonate and saturated saline, dried over anhydrous sodium sulfate and then distilled to remove the solvent. The residue was subjected to column chromatography and eluted with a mixed solvent of ethyl acetate and n-hexane. The solvent was then distilled off, whereby 3.89 g (yield: 55%) of Compound 2 was obtained.

Test 1

Inhibition Test on Neutral Endopeptidase Activity of Cultivated Human Fibroblast Normal human fibroblast commercially available from Dainippon Pharmaceutical Co., Ltd. was subcultured on a DME medium containing 10% bovine fatal serum and provided for the present test. The cells peeled by a rubber-policeman from a Petri dish were floated in a phosphate-buffered physiological saline, collected by a low-velocity centrifuge, and washed three times with the same physiological saline. The cells were floated in a 0.1% Triton X-100/0.2M tris-HCl buffer (pH 8.0), followed by ultrasonic pulverization, whereby an enzyme solution was obtained.

The enzyme activity was measured as follows: To 100 μL of an MES buffer (100 mM, pH 6.5) added with sodium chloride (300 mM), were added 2 μL of the enzyme solution, 1 μL of a solution of the invention compound and, as a substrate for the measurement of enzyme activity, 1 μL of 20 mM glutalyl-Ala-Ala-Phe-4-methoxy-2-naphthylamine, followed by reaction at 37° C. for 1 hour. Phosphoramidon was added to the reaction mixture to give its final concentration of 0.4 μM and then, the reaction was terminated. Aminopeptidase M having a final concentration of 20 mU was added to the reaction mixture and the resulting mixture were reacted at 37° C. for 15 minutes. The amount of the resulting 4-methoxy-2-naphthylamine was determined by measuring the fluorescent strength at excited wavelength of 340 nm and fluorescent wavelength of 425 nm by a fluorospectrophotometer and % inhibition of the compound against enzyme activity was determined. Results are shown in Table 2.

Table 2

| Test substance | Concentration | % inhibition |
|---|---|---|
| Compound 8 | 1 mM | 23.8 ± 2.7 |
| Compound 9 | 0.1 mM | 74.5 ± 9.3 |
| Compound 10 | 0.1 mM | 91.2 ± 3.7 |
| Compound 11 | 0.1 mM | 85.7 ± 2.2 |
| Compound 12 | 0.1 mM | 69.5 ± 4.3 |
| Compound 13 | 1 mM | 49.3 ± 1.2 |
| Phe-Gly | 1 mM | 49.4 |
| Phe-β-Ala | 0.1 mM | 92.6 |
| Phe-Phe | 1 mM | 85.7 |
| Phe-Leu | 1 mM | 72.9 |
| Phe-Ala | 1 mM | 75.3 |
| Phe-Asp | 1 mM | 85.4 |
| Aspartame | 1 mM | 30.2 |
| Asp-Phe | 1 mM | 45.7 |

Example 1

Hair Growth Test (1) Using Mice

Each of the test substances was dissolved or suspended in an extraction solvent to give a concentration as shown in Table 3, whereby the corresponding hair growth inhibitor was prepared. The back of each of 49-day-old C3H/HeNCrj mice (one group consisting of 20 mice) was shaved by 2×4 cm$^2$ by electric clippers and an electric shaver so as not to injure its skin. From the next day, the inhibitor was applied by 20 μL/once/day to the shaved portion for 4 weeks, while only the solvent was applied to a control group. In order to observe hair regrowth, the picture of the shaved portion was taken at a fixed magnification and the day-dependent change of the area ratio of the regrowth hair (regrowth hair area/shaved area) was measured by an image analyzer.

As a result, apparent from Table 3, it has been found that the composition of the present invention exhibited excellent hair growth inhibitory action.

Test 3

| Test substance | Concentration (dry solids content) | Hair growth inhibition ratio (%) 3 weeks after depilation |
|---|---|---|
| Malt extract | 0.136% | 48.6 |
| *Juniperus virginiana* L. extract | 0.062% | 36.1 |
| *Juniperus communis* extract | 0.075% | 30.5 |
| Burnet extract | 0.270% | 58.5 |
| Malt extract + burnet extract | 0.136% + 0.270% | 72.3 |
| *Juniperus virginiana* L. extract + burnet extract | 0.062% + 0.270% | 63.9 |
| Malt extract + *Juniperus virginiana* L. extract + burnet extract | 0.136% + 0.062% + 0.270% | 82.4 |

Example 2

Hair Growth Test (2) Using Mice (1) Preparation of a Test Sample

Component (B)

Each of Compounds 1 to 3 and 7 was dissolved in a 50% ethanol solution, whereby a 1 mM solution was prepared.

Compound (C)

Papain powder (produced by CALBIOCHEM-NOVABIOCHEM CORPORATION) was dissolved in purified water to prepare a 2% aqueous solution, followed by the addition of an equal amount of ethanol to prepare a 1% ethanol solution.

Trypsin powder (produced by Sigma Aldrich Corporation) was dissolved in Hanks' Balanced Salt Solution (produced by Gibco BRL) having 1 mM EDTA-4Na dissolved therein, followed by the addition of an equal amount of ethanol to prepare a 1% ethanol solution.

Chymotrypsin powder (produced by Sigma Aldrich Corporation) was treated in a manner similar to that employed for trypsin, whereby a 1% ethanol solution was prepared.

The above-described components (B) and (C) were combined as shown in Table 4 as a test sample.

(2) Testing Method

The back of 6-week-old C3H mice (each group consisting of 5 mice) was shaved by 2×4 cm$^2$ by electric hair clippers or an electric shaver so as not to injure its skin. The sample was applied in an amount of 100 μL/once to the shaved portion twice a day for 4 weeks. To a control group, only a solvent was applied. Three weeks after depilation, the picture of the shaved portion was taken at a fixed magnification in order to observe the regrowth hair and the area of the hair regrowth (area of regrowth hair/shaved area) was compared with that of the control group by using an image analyzer. The results are shown in Table 4.

TABLE 4

| Test sample | Concentration applied | Hair growth inhibition 3 weeks after depilation | | | |
|---|---|---|---|---|---|
| | | Solvent | Papain 1% | Trypsin 1% | Chymotrypsin 1% |
| Solvent | | 0 | 17.3 | 25.6 | 20.1 |
| Compound 1 | 1 mM | 58.7 | 77.5 | 84.7 | 80.2 |
| Compound 2 | 1 mM | 59.1 | 80.3 | — | — |
| Compound 3 | 1 mM | 64.8 | 83.6 | 88.5 | — |
| Compound 7 | 1 mM | 59.7 | 77.9 | — | — |

As apparent from Table 4, the test sample containing the elastase inhibitor as the component (B) and proteolytic enzyme as the component (C) in combination exhibited excellent hair growth inhibiting effects.

Example 3

Hair Growth Inhibiting Lotion

| | | (wt. %) |
|---|---|---|
| (i) | Polyoxyethylene hydrogenated castor oil | 0.8 |
| | Ethanol | 30.0 |
| (ii) | Malt extract | 0.1 (dry solids content) |
| | Sodium dodecyl sulfate | 0.12 |
| | Dodecyl methylamine oxide | 0.18 |
| | Isopropyl alcohol | 15.0 |
| | Benzyl alcohol | 15.0 |
| | Glycerin | 2.0 |
| | Purified water | Balance |

Components belonging to (i) and those belonging to (ii) were dissolved, respectively. To (i) was added (ii), followed by uniform mixing under stirring, whereby a hair growth inhibiting lotion was obtained.

Example 4

Hair Growth Inhibiting Cream

| | | (wt. %) |
|---|---|---|
| (i) | Liquid paraffin | 10.0 |
| | Squalane | 7.0 |
| | Jojoba oil | 3.0 |
| | Solid paraffin | 3.0 |
| | Polyoxyethylene cetyl ether | 2.0 |
| | Sorbitan sesquioleate | 1.0 |
| | Potassium hydroxide | 0.1 |
| (ii) | *Juniperus virginiana* L. | 0.01 (dry solids content) |
| | Glycerin | 3.0 |
| | Ethyl paraben | 0.1 |
| | Purified water | Balance |

Components belonging to (i) and components belonging to (ii) were dissolved under heating, respectively. To (i) was added (ii), followed by uniform mixing under stirring. The resulting mixture was emulsified and cooled, whereby a hair growth inhibiting cream was obtained.

Example 5

Hair Growth Inhibiting Foam

| | | (wt. %) |
|---|---|---|
| (i) | Malt extract | 0.1 (dry solids content) |
| | Cetanol | 0.1 |
| | Propylene glycol | 2.0 |
| | Dimethyl silicone oil | 2.0 |
| | Polyoxyethylene hydrogenated castor oil | 2.5 |
| | Liquid paraffin | 1.0 |
| | Polyvinyl pyrrolidone | 0.5 |
| | Methyl paraben | 0.2 |
| | Ethanol | 10.0 |
| | Purified water | Balance |
| (ii) | Liquefied petroleum gas (propellant) | 4.0 |

After uniform mixing of the components belonging to (i), the resulting mixture was filled in a container. The component (ii) was then filled in the container in a conventional manner, whereby a hair growth inhibiting foam was prepared.

Example 6

Aerosol

| | | (wt. %) |
|---|---|---|
| (i) | *Juniperus virginiana* L. | 0.01 (dry solids content) |
| | Cetanol | 1.2 |
| | Propylene glycol | 4.0 |
| | Ethanol | 8.0 |
| | Purified water | balance |
| (ii) | Liquefied petroleum gas (propellant) | 4.0 |

After uniform mixing of the components belonging to (i), the resulting mixture was filled in a container. The component (ii) was then filled in the container in a conventional manner, whereby an aerosol was prepared.

Example 7

Hair Growth Inhibiting Lotion

The components belonging to (i) and the components belonging to (ii) were dissolved, respectively. To (i) was added (ii), followed by uniform mixing under stirring, whereby a hair growth inhibiting lotion was obtained.

| | | (wt. %) |
|---|---|---|
| (i) | Polyoxyethylene hydrogenated castor oil | 0.8 |
| | Ethanol | 30.0 |
| (ii) | Compound 6 | 1.0 |
| | Papain | 1.0 |
| | Lactic acid | 2.0 |
| | Sodium dodecyl sulfate | 0.12 |
| | Dodecylmethylamine oxide | 0.18 |
| | Isopropyl alcohol | 15.0 |
| | Benzyl alcohol | 15.0 |
| | Glycerin | 2.0 |
| | Purified water | Balance |

Example 8

Hair Growth Inhibiting Cream

The components belonging to (i) and the components belonging to (ii) were dissolved under heating, respectively. To (i) was added (ii), followed by uniform mixing under stirring. After emulsification, the emulsion was cooled, whereby a hair growth inhibiting cream was obtained.

|  |  | (wt. %) |
|---|---|---|
| (i) | Liquid paraffin | 10.0 |
|  | Squalane | 7.0 |
|  | Jojoba oil | 3.0 |
|  | Solid paraffin | 3.0 |
|  | Polyoxyethylene cetyl ether | 2.0 |
|  | Sorbitan sesquioleate | 1.0 |
|  | Potassium hydroxide | 0.1 |
| (ii) | Compound 7 | 1.0 |
|  | Trypsin enclosed in liposome | 2.0 |
|  | Glycolic acid | 2.0 |
|  | Calcium thioglycolate | 0.5 |
|  | Glycerin | 3.0 |
|  | Ethyl paraben | 0.1 |
|  | Purified water | Balance |

Example 9

Hair Growth Inhibiting Foam

The components belonging to (i) were uniformly mixed and filled in a container. The container was then filled with (ii) in a conventional manner, whereby a hair growth inhibiting foam was prepared.

|  |  | (wt.%) |
|---|---|---|
| (i) | Compound 5 | 1.0 |
|  | Chymotrypsin | 1.0 |
|  | Salicylic acid | 1.0 |
|  | Calcium thioglycolate | 0.5 |
|  | Cetanol | 0.1 |
|  | Propylene glycol | 2.0 |
|  | Dimethyl silicone oil | 2.0 |
|  | Polyoxyethylene hydrogenated castor oil | 2.5 |
|  | Liquid paraffin | 1.0 |
|  | Polyvinyl pyrrolidone | 0.5 |
|  | Methyl paraben | 0.2 |
|  | Ethanol | 10.0 |
|  | Purified water | Balance |
| (ii) | Liquefied petroleum gas (propellant) | 4.0 |

What is claimed is:

1. A method of inhibiting hair growth comprising administering to a surface of skin in need thereof an effective amount of (B) an elastase inhibitor and (C) at least one proteolytic enzyme selected from the group consisting of papain, trypsin, chymotrypsin, pepsin, bromelain, ficin and pancreatin.

2. The method of inhibiting hair growth of claim 1, wherein said component (C) is papain.

3. The method of inhibiting hair growth of claim 1, wherein said component (C) is trysin.

4. The method of inhibiting hair growth of claim 1, wherein said component (C) is chymotrypsin.

5. The method of inhibiting hair growth of claim 1, wherein said component (C) is pepsin.

6. The method of inhibiting hair growth of claim 1, wherein said component (C) is bromelain.

7. The method of inhibiting hair growth of claim 1, wherein said component (C) is ficin.

8. The method of inhibiting hair growth of claim 1, wherein said component (C) is pancreatin.

* * * * *